United States Patent [19]
Keimel

[11] Patent Number: 5,163,427
[45] Date of Patent: Nov. 17, 1992

[54] APPARATUS FOR DELIVERING SINGLE AND MULTIPLE CARDIOVERSION AND DEFIBRILLATION PULSES

[75] Inventor: John G. Keimel, New Brighton, Minn.

[73] Assignee: Medtronic, Inc., Minneapolis, Minn.

[21] Appl. No.: 612,758

[22] Filed: Nov. 14, 1990

[51] Int. Cl.⁵ .................................................. A61N 1/39
[52] U.S. Cl. ............................................... 128/419 D
[58] Field of Search ................................... 128/419 D

[56] References Cited

U.S. PATENT DOCUMENTS

| | | | |
|---|---|---|---|
| 3,614,954 | 10/1971 | Mirowski et. al. | 128/419 D |
| 4,291,699 | 9/1981 | Geddes et al. | 128/419 D |
| 4,566,457 | 1/1986 | Stemple | 128/419 D |
| 4,641,656 | 2/1987 | Smits | 128/419 D |
| 4,708,145 | 11/1987 | Tacker, Jr. et al. | 128/419 D |
| 4,727,877 | 3/1988 | Kallok | 128/419 D |
| 4,800,883 | 1/1989 | Winstrom | 128/419 D |
| 4,932,407 | 6/1990 | Williams | 128/419 D |
| 4,953,551 | 9/1990 | Mehra et al. | 128/419 D |

Primary Examiner—Kyle L. Howell
Assistant Examiner—Scott M. Getzow
Attorney, Agent, or Firm—Reed A. Duthler; Harold R. Patton

[57] ABSTRACT

An implantable cardioverter having circuitry for generating high energy cardioversion and defibrillation pulses. The output circuitry is so configured that it may provide simultaneous pulse, multiple electrode; sequential pulse, multiple electrode; or single pulse, two electrode defibrillation and/or cardioversion pulse regimens. The output circuitry is configured to allow delivery of energy sequentially from two capacitor banks during sequential pulse regimens and to deliver the energy stored in both capacitor banks simultaneously during simultaneous pulse, multiple electrode and single pulse, two electrode defibrillation pulse regimens.

6 Claims, 4 Drawing Sheets

APPARATUS FOR DELIVERING SINGLE AND MULTIPLE CARDIOVERSION AND DEFIBRILLATION PULSES

BACKGROUND OF THE INVENTION

This invention relates generally to implantable medical stimulators, and more particularly to implantable cardioverters and defibrillators.

Initially, implantable cardioverters and defibrillators were envisioned as operating with a single pair of electrodes applied on or in the heart. Examples of such systems are disclosed in U.S. Pat. No. 3,614,954 by Mirowski et al., in which pulses are delivered between an electrode placed in the right ventricle, and a second electrode placed outside the right ventricle. Studies have indicated that two electrode defibrillation systems often require undesirably high energy levels to effect defibrillation. In an effort to reduce the amount of energy required to effect defibrillation, numerous suggestions have been made with regard to multiple electrode systems. For example, sequential pulse multiple electrode systems are disclosed in U.S. Pat. No. 4,291,699, issued to Geddes et al., in U.S. Pat. No. 4,708,145, issued to Tacker et al., in U.S. Pat. No. 4,727,877 issued to Kallok and in U.S. Pat. No. 4,932,407 issued to Williams. Sequential pulse systems operate based on the assumption that sequential defibrillation pulses, delivered between differing electrode pairs have an additive effect such that the overall energy requirements to achieve defibrillation are less than the energy levels required to accomplish defibrillation using a single pair of electrodes.

An alternative approach to multiple electrode, sequential pulse defibrillation is disclosed in U.S. Pat. No. 4,641,656 issued to Smits and also in the above-cited Williams patent. This defibrillation method may conveniently be referred to as multiple electrode, simultaneous pulse defibrillation, and involves the delivery of defibrillation pulses simultaneously between two different pairs of electrodes. For example, one electrode pair may include a right ventricular electrode and a coronary sinus electrode, and the second electrode pair may include a right ventricular electrode and a subcutaneous patch electrode, with the right ventricular electrode serving as a common electrode to both electrode pairs. An alternative multiple electrode, simultaneous pulse system is disclosed in U.S. Pat. No. 4,953,551, issued to Mehra et al., employing right ventricular, superior vena cava and subcutaneous patch electrodes.

In the above-cited prior simultaneous pulse, multiple electrode systems, delivery of the simultaneous defibrillation pulses is accomplished by simply coupling two of the electrodes together. For example, in the above-cited Mehra patent, the superior vena cava and subcutaneous patch electrodes are electrically coupled, and a pulse is delivered between these two electrodes and the right ventricular electrode. Similarly, in the above-cited Williams patent, the subcutaneous patch and coronary sinus electrodes are electrically coupled, and a pulse is delivered between these two electrodes and a right ventricular electrode.

SUMMARY OF THE INVENTION

The present invention provides a pulse generator for use in conjunction with an implantable cardioverter/defibrillator which is capable of providing all three of the defibrillation pulse methods described above, with a minimum of control and switching circuitry. The output stage is provided with two separate capacitor banks, which are sequentially discharged during sequential pulse defibrillation and simultaneously discharged during single or simultaneous pulse defibrillation. The output circuitry avoids the necessity of "Y" connectors or other external bridging apparatus to couple electrodes together during delivery of simultaneous pulse regimens, which would preclude their use in delivering sequential pulse regimes absent physical modification of the electrode system.

The output circuitry of the present invention is primarily responsive to two control signals from the implantable defibrillator. A first control signal triggers discharge of the first capacitor bank between first and second electrodes. A second control signal triggers discharge of both capacitor banks between a third electrode and the first electrode. Simply by modifying the number and time order of the control signals, it is possible to select between the three defibrillation pulse regimes discussed above.

For example, sequential activation of the first and second control signals will result in delivery of a sequential pulse regime. Simultaneous activation of the control signals will result in delivery of a simultaneous pulse regime, and activation of only the first or the second control signal provides for delivery of a single pulse, two electrode defibrillation pulse regime. No additional switching circuitry is required internal or external to the defibrillator to select the electrode and pulse configuration required.

The output circuitry of the present invention has the advantage that the second control signal, triggering discharge of both capacitor banks, allows for the delivery of the same amount of energy during a single pulse, two electrode defibrillation pulse regimen as during the simultaneous multi-electrode defibrillation regimen or a sequential pulse regimen. This feature is believed especially desirable in that it allows for a minimization of the size and number of capacitors required to give the implantable cardioverter the flexibility to deliver all three pulse regimens.

DETAILED DESCRIPTION OF THE PREFERRED EMBODIMENT

Figure 1:
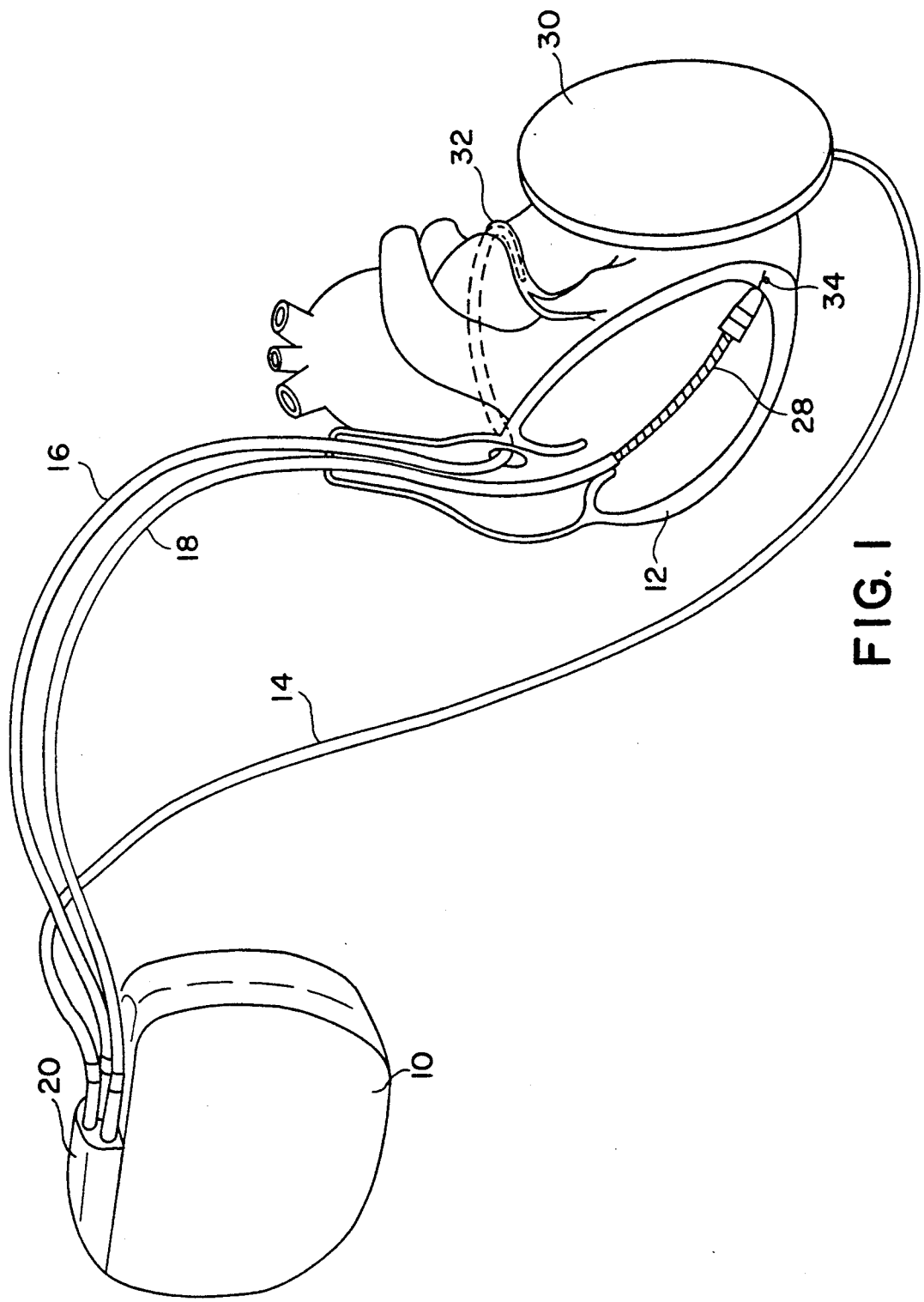
FIG. 1 is a drawing illustrating the physical components of a cardioverter and cardioversion lead system of the type in which the present invention may be advantageously practiced.

FIG. 1 illustrates an implantable pacemaker/cardioverter/defibrillator 10, its associated electrical leads 14, 16 and 18, and their relationship to a human heart 12. The leads are coupled to the pacemaker/cardioverter/defibrillator 10 by means of a multi-lumen connector block 20, which contains separate connector ports for each of the three leads illustrated. Lead 14 is coupled to a subcutaneous electrode 30, which is intended to be mounted subcutaneously in the region of the left chest. Lead 16 is a coronary sinus lead employing an elongated coil electrode which is located in the coronary sinus and great vein region of the heart. The location of the electrode is illustrated in broken line format at 32, and extends around the heart from a point within the opening of the coronary sinus to a point in the vicinity of the left atrial appendage.

Lead 18 is provided with an elongated electrode coil 28 which is located in the right ventricle of the heart. Lead 18 also includes a stimulation electrode 34 which takes the form of an advanceable helical coil which is screwed into the myocardial tissue of the right ventricle. Lead 18 may also include one or more additional electrodes for near and far field electrogram sensing. A more detailed description of the leads illustrated can be found in U.S. Pat. No. 4,932,407 issued to Williams, on Jun. 12, 1990, incorporated herein by reference in its entirety. However, the invention is also believed workable in the context of multiple electrode systems employing different sets of electrodes, including superior vena cava electrodes and epicardial patch electrodes.

In the system illustrated, cardiac pacing pulses are delivered between helical electrode 34 and elongated electrode 28. Electrodes 28 and 34 are also employed to sense electrical signals indicative of ventricular contractions. As illustrated, it is anticipated that the right ventricular electrode 28 will serve as the common electrode during sequential and simultaneous pulse multiple electrode defibrillation regimens. For example, during a simultaneous pulse defibrillation regimen, pulses would simultaneously be delivered between electrode 28 and electrode 30 and between electrode 28 and electrode 32. During sequential pulse defibrillation, it is envisioned that pulses would be delivered sequentially between subcutaneous electrode 30 and electrode 28 and between coronary sinus electrode 32 and right ventricular electrode 28. Single pulse, two electrode defibrillation pulse regimens may be also provided, typically between electrode 28 and coronary sinus electrode 32. Alternatively, single pulses may be delivered between electrodes 28 and 30. The particular interconnection of the electrodes to the implantable pacemaker/cardioverter/-defibrillator will depend somewhat on which specific single electrode pair defibrillation pulse regimen is believed more likely to be employed.

Figure 2:
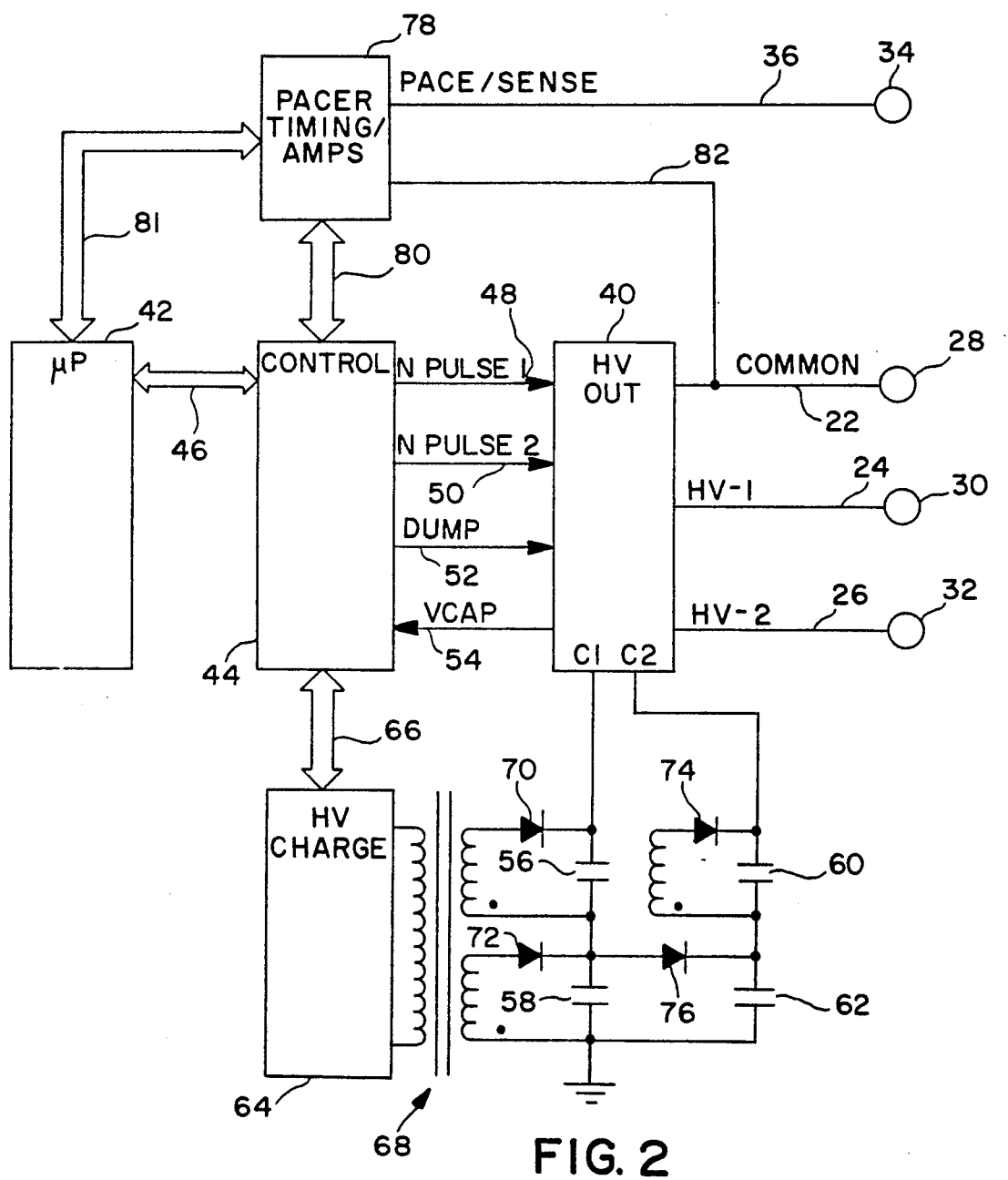
FIG. 2 is a block functional diagram illustrating the interconnection of the improved output circuitry of the present invention with the primary functional components of an implantable cardioverter/pacemaker.

FIG. 2 is a block diagram illustrating the interconnection of an output circuit 40 according to the present invention with a prior art implantable pacemaker/cardioverter/defibrillator. As illustrated, the device is controlled by means of a stored program in a microprocessor 42, which performs all necessary computational functions within the device. Microprocessor 42 is linked to control circuitry 44 by means of a bi-directional data/control bus 46, and thereby controls operation of the output circuitry 40 and the high voltage charging circuitry 64. On reprogramming of the device or on the occurrence of signals indicative of delivery of cardiac pacing pulses or of the occurrence of cardiac contractions, pace/sense circuitry 78 will awaken microprocessor 42 to perform any necessary mathematical calculations, to perform tachycardia and fibrillation detection procedures and to update the time intervals controlled by the timers in pace/sense circuitry 78. The basic operation of such a system in the context of an implantable pacemaker/cardioverter/defibrillator may correspond to any of the systems known to the art, and in more particular may correspond generally to those illustrated in U.S. Pat. No. 4,548,209, issued to Wielders, et al., U.S. Pat. No. 4,693,253, issued to Adams, U.S. Pat. No. 4,375,817, issued to Engle, et al, U.S. Pat. No. 4,384,585, issued to Zipes, or U.S. Pat. No. 4,830,006, issued to Haluska, et al, all of which are incorporated herein by reference in their entireties.

The control circuitry 44 provides three signals of primary importance to the output circuitry 40 of the present invention. These include the first and second control signals discussed above, labeled here as NPULSE-1, line 48, and NPULSE-2, line 50. Also of importance is DUMP line 52 which initiates discharge of the output capacitors and VCAP line 54 which provides a signal indicative of the voltage stored on the output capacitors 56, 58, 60, 62, to the control circuitry 44. The defibrillation electrodes 28, 30 and 32 illustrated in FIG. 1, above, are shown coupled to the output circuitry 40 by means of conductors 22, 24 and 26. For ease of understanding, these conductors are also labeled as "COMMON", "HV-1" and "HV-2". However, other configurations are also possible. For example, subcutaneous electrode 30 may be coupled to HV-2 conductor 26, to allow for a single pulse regimen to be delivered between electrodes 28 and 30. As discussed in the Summary of the Invention section, during a logic signal on NPULSE-1 line 48, a pulse is delivered between electrode 30 and electrode 28. During a logic signal on NPULSE-2 line 50, a defibrillation pulse is delivered between electrode 32 and electrode 28.

The output circuitry of the present invention includes two capacitor banks, used for delivering defibrillation pulses to the electrodes. The first capacitor bank includes capacitors 56 and 58. The second capacitor bank includes capacitors 60 and 62. In FIG. 2, these capacitors are illustrated in conjunction with the high voltage charging circuitry 64, controlled by the control/timing circuitry 44 by means of a bi-directional control/data bus 66. As illustrated, capacitors 56, 58, 60 and 62 are charged by means of a high frequency, high voltage transformer 68. Proper charging polarities are maintained by means of diodes 70, 72 and 74. VCAP line 54 provides a signal indicative of the voltage on the capacitor banks, and allows for control of the high voltage charging circuitry and for termination of the charging function when the stored voltage equals the programmed charging level. The details of the high voltage charging circuitry are not believed to be critical with regard to practicing the present invention. However, the circuitry illustrated is believed desirable in conjunction with the present invention as the disclosed configuration of the charging circuitry allows for equal charging of all four capacitors within the banks.

Pace/sense circuitry 78 includes an R-wave amplifier according to the prior art, or more advantageously as disclosed in co-pending, commonly assigned application Ser. No. 07/612,760 by Keimel et al. for an "Apparatus for Monitoring Electrical Physiological Signals", filed as of the date of the present invention. This application is incorporated herein by reference in its entirety. However, the present invention is believed workable in the context of any known R-wave amplification system. Pace/sense circuitry 78 also includes a pulse generator for generating cardiac pacing pulses, which may also correspond to any known cardiac pacemaker output circuitry and includes timing circuitry for defining ventricular pacing intervals, refractory intervals and blanking intervals, under control of microprocessor 42 via control/data bus 81. Control signals triggering generation of cardiac pacing pulses by pace/sense circuitry 78 and signals indicative of the occurrence of R-waves, from pace/sense circuitry 78 are communicated to control circuitry 44 by means of a bi-directional data bus 81. Pace/sense circuitry 78 is coupled to helical electrode 34 illustrated in FIG. 1 by means of a conductor 36. Pace/sense circuitry 78 is also coupled to ventricular electrode 28, illustrated in FIG. 1, by means of a conductor 82, allowing for bipolar sensing of R-waves between electrodes 34 and 28 and for delivery of bipolar pacing pulses between electrodes 34 and 28, as discussed above.

Figure 3:
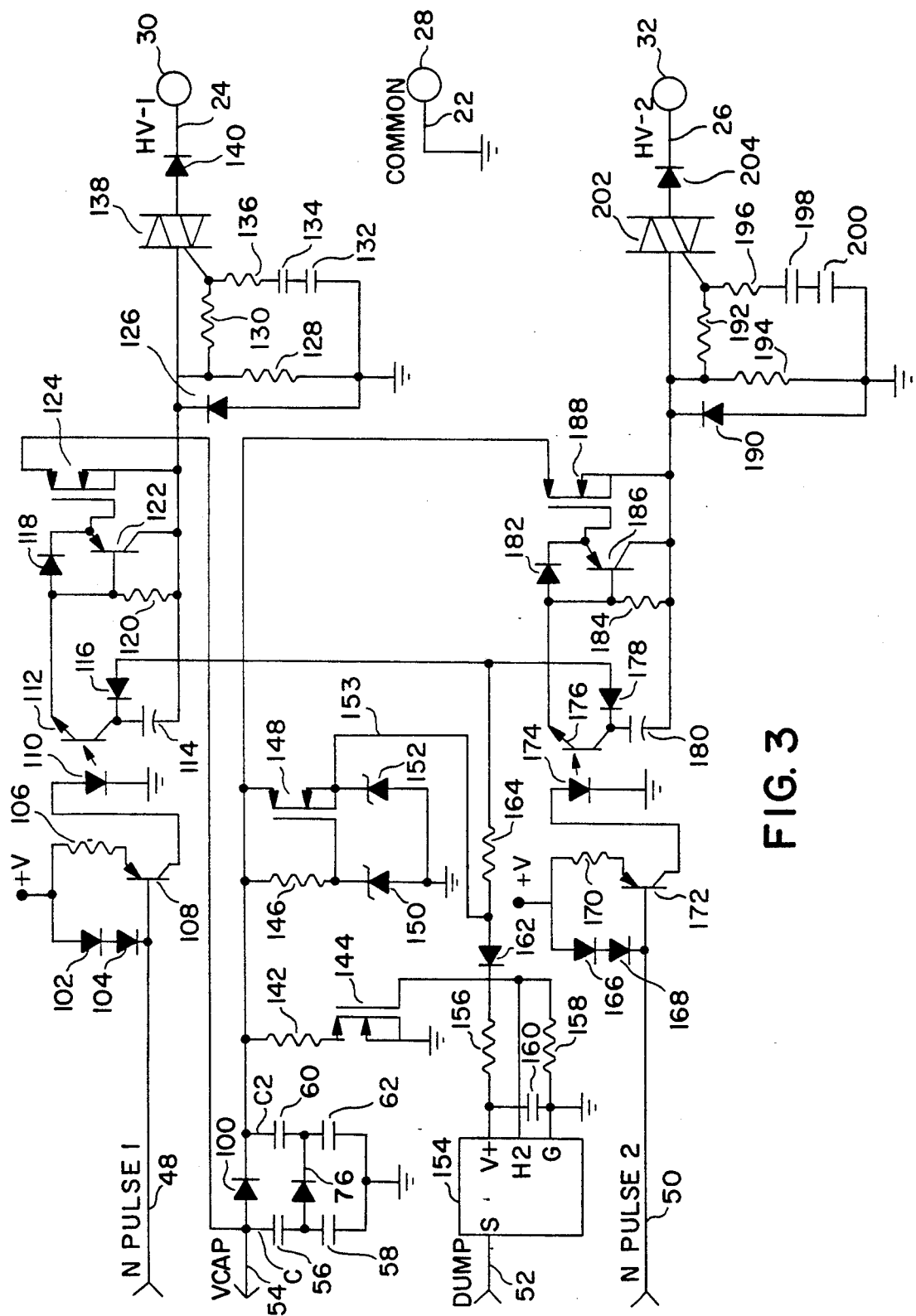
FIG. 3 is a circuit schematic of a specific embodiment of an output circuit according to the present invention.

FIG. 3 is a detailed schematic illustrating a specific embodiment of the output circuitry 40, and its interconnection to the capacitor banks. The charging circuitry is omitted from this diagram for the sake of clarity, but should be presumed to be as illustrated in FIG. 2. Inputs to the circuitry include NPULSE-1 line 48, NPULSE-2 line 50 and DUMP line 52. The outputs from the circuitry include VCAP line 54, HV-1 line 24 and HV-2 line 26, all of which correspond to identically labeled structures in FIG. 2. The capacitors 56, 58, 60 and 62 as well as diode 76 also correspond to those illustrated in FIG. 2. Diode 100 is located within output circuitry 40, and plays an important role in allowing for the selection of single and multiple pulse defibrillation regimens by means of the control signals on NPULSE-1 line 48 and NPULSE-2 line 50, as will be discussed below.

FET 148 in conjunction with zeiner diodes 150 and 152 and resistor 146 provide a 14 volt power source which is used for driving the output FETs 124 and 188 and for driving the dump FET 144. Capacitor 160 is charged via line 153, coupled through diode 162 and resistor 156. Capacitor 114 is charged via line 153, coupled through resistor 164 and diode 116. Capacitor 180 is similarly charged via line 153, coupled through resistor 164 and diode 178. The charge stored on capacitors 114, 180 and 160 is used to provide a drive signal to the output FETs 124 and 188 and to the dump FET 144, respectively.

On receipt of a high logic signal on DUMP line 52, voltage converter 154 provides a drive signal to dump FET 144, using the energy stored in capacitor 160, allowing for discharge of the energy stored in both capacitor banks (56,58,60,62) through resistor 142 and FET 144. A high logic signal on line 52 is provided in the event that a tachyarrhythmia is detected but terminates prior to delivery of a high voltage cardioversion or defibrillation pulse, allowing the energy stored on capacitors 56, 58, 60, 62 to be discharged. Similarly, it is envisioned that a signal on line 52 may be initiated in response to a telemetered external control signal, allowing for internal dumping of the output capacitors.

Operation of the circuitry to provide single and multiple pulse defibrillation pulse regimens is dependent upon the occurrence of and the time order of low logic signals on NPULSE-1 line 48 and NPULSE-2 line 50. In the presence of a low logic signal on line 48, LED 100 is activated via drive circuitry comprising diodes 102 and 104, resistor 106 and transistor 108. Diode 110 is part of an optical isolator, and its output serves to enable current flow through phototransistor 112, from capacitor 114, which was previously charged as discussed above. This turns on FET 124 via diode 118, allowing passage of voltage stored on capacitors 56 and 58 therethrough. Transistor 122 and resistor 120 assist in assuring rapid turn off of FET 124, after cessation of the negative logic signal on NPULSE-1 line 48. The voltage stored on capacitors 56 and 58 is passed through to electrode 30 by means of triac 138. Rapid switching of triac 138 is facilitated by the associated circuitry including resistors 130 and 128, resistor 136 and capacitors 132 and 134.

The duration of the low logic signal on NPULSE-1 line 48 may be determined by a timer located within control/timing circuitry 44. Alternatively, the low logic signal on line 48 may terminate upon the voltage level on capacitors 56 and 58 reaching a predetermined value, as indicated by the voltage on VCAP line 54. Either mechanism of controlling pulse duration is workable in the context of the illustrated output circuit. If a multiple pulse defibrillation regimen is desired, NPULSE-1 line 48 will be used to trigger the initial pulse. This allows for discharge of energy stored in only capacitors 56 and 58.

A low logic signal on NPULSE-2 line 50 triggers delivery of defibrillation energy to electrode 32, through circuitry corresponding to that discussed above. Diodes 166 and 168 in conjunction with resistor 170 and transistor 172 provide a drive signal for LED 174, which allows discharge of capacitor 180 through phototransistor 176, turning on FET 188 to allow passage of energy stored in capacitors 60 and 62 through to triac 202, and then to electrode 32 via diode 204. As in the case of the circuitry above, transistor 186 and 184 assist in rapid shut off of FET 188. Resistors 192, 194 and 196 and capacitors 198 and 200 assist in rapid switching of triac 202.

Diodes 140 and 204 protect the output circuitry from positive voltages on the HV-1 and HV-2 conductors. Diodes 126 and 190 protect the output circuitry under circumstances when the HV-1 and HV-2 conductors are driven negative with respect to the COMMON conductor, for example, due to transthoracic defibrillation shocks or due to electro-cautery.

It is in conjunction with the defibrillation pulse triggered by a low logic signal on NPULSE-2 line 50 that diode 100 becomes significant. For example, assuming that a sequential pulse regimen has been selected, after discharge of capacitors 56 and 58, the voltage on capacitors 60 and 62 will remain at their initial charge levels. During discharge of capacitors 60 and 62, during the second defibrillation pulse, their charge level may be reduced to a level greater than one diode drop below the charge remaining on capacitors 56 and 58. In this case, during the later portion of the second pulse, energy stored in capacitors 56 and 58 is available for delivery. Similarly, in the event that only a single pulse is desired, this would be triggered by a low signal on NPULSE-2 line 50, without a preceding signal on NPULSE-1 line 48. In this case, initial discharge would be from capacitors 60 and 62, but as soon as their voltage level fell to less than one diode drop below the voltage stored on capacitors 56 and 58, energy stored in all four capacitors 56, 58, 60, 62 would become available for delivery during the pulse. This circuitry thus provides the capability of delivering a single pulse having substantially greater energy than the individual pulses used in a sequential pulse regimen. In the event that a simultaneous pulse regimen is desired, simultaneous low logic signals on end pulse 1 line 48 and end pulse 2 line 50 are applied. In this case, all four capacitors are discharged with capacitors 56 and 58 discharging primarily through electrode 30 and capacitors 60 and 62 discharging through electrode 32. In this context, diode 100 prevents the voltage of the pulse delivered between electrodes 32 and 28 from being less than one diode drop below the voltage of the pulse delivered between electrodes 30 and 28.

Figure 4:
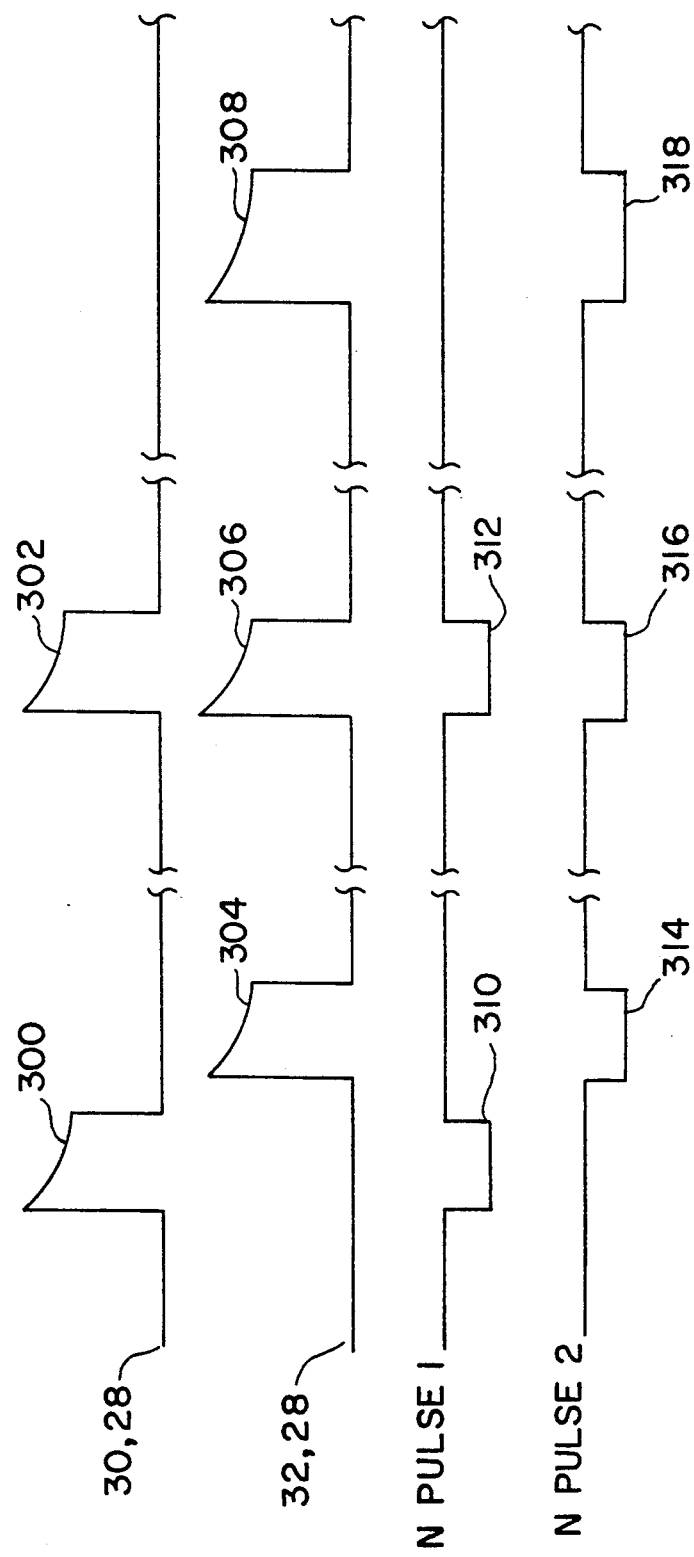
FIG. 4 is a timing diagram illustrating the relationship between the control signals from the implantable cardioverter illustrated in FIG. 2, and the output pulses to the electrode system illustrated in FIG. 1.

FIG. 4 is a timing chart illustrating the functional inter-relationship of the control signals on NPULSE-1 line 48 and NPULSE-2 line 50 and the pulses provided between the various electrodes. FIG. 4 illustrates the sequential pulse multiple electrode regimen, the simultaneous pulse multiple electrode regimen, and the single pulse, two electrode regimen, in that order.

The sequential pulse multiple electrode regimen is illustrated first, with the initial pulse 300 delivered between electrodes 28 and 30, in response to a low logic signal 310 on NPULSE-1 line 48. The second pulse 304 is delivered between electrodes 32 and 28 and is triggered in response a low logic level signal 314 on NPULSE-2 line 50. The simultaneous, multiple electrode pulse regimen is illustrated next with pulses 302 delivered between electrode pair 38 and 28 and pulse 306 delivered simultaneously between electrode pair 32 and 28. The output pulses are delivered in response to simultaneous low signals 312 and 316 on NPULSE-1 line 48 and NPULSE-2 line 50, respectively. The two electrode, single pulse regimen is illustrated last. Here, a single pulse 308 delivered between electrodes 32 and 28 is triggered in response to a low logic signal 318 on NPULSE 2 line 50. As illustrated, the low logic level signal 318 extends for a longer time duration then the corresponding signals 314 and 316 provided in conjunction with the sequential and simultaneous pulse regimens. The cardioversion pulse 308 is shown for extending for a similar time period, with the tilt of the pulse (the voltage differential between the beginning and end of the pulse, divided by the peak voltage) being approximately equal to that illustrated in conjunction with corresponding pulses 304 and 306. This is made possible by the fact that all four of the capacitors are being employed to deliver the defibrillation pulse 308, so that it may maintain a high pulse amplitude for a greater time duration than either of the individual pulses generated during the sequential pulse regimen described earlier. In the event that the pulse duration is determined by a tilt limitation, the result will be a longer pulse than delivered between the same electrodes during sequential pulse regimens. In the event that the duration of stimulation pulse is a predetermined time interval, it will allow the pulse to remain at a higher amplitude for a longer period of time, as a function of the overall increased energy made available by the present invention, for use in the two electrode, single pulse regimen.

The output circuitry described is particularly advantageous in the context of an implantable cardioverter/defibrillator. In such devices, the output capacitors typically occupy a substantial volume of the device, and minimization of the volume of these capacitors is of paramount importance in reducing the overall size of the implantable device. The disclosed circuitry, by allowing the combination of both capacitor banks used during sequential and simultaneous pulse regimes to deliver a single output pulse is believed to represent the most efficient available method for storing energy while retaining the flexibility to perform all three pulse regimens described. Moreover, the circuit allows for the selection of multiple defibrillation pulse regimes without the necessity of intricate or complicated switching circuitry for rerouting the energy stored in the capacitors to provide single or multiple pulse regimens. This allows for a minimalization of the number of high current FETs, SCRs, or triacs that might otherwise be required.

The output circuitry is also valuable in those cases in which the device is implanted with only two defibrillation electrode leads. In such case, an insulative plug would be installed in the connector block in the receptacle normally used for coupling to HV-1 line 24. The device would normally be programmed to generate control signals only on NPULSE-2 line 50. However, even if the device is reprogrammed after implant in an attempt to deliver a sequential pulse regimen, there is no adverse effect. Because HV-1 line 24 is unconnected, no energy will be discharged in response to a control signal on NPULSE-1 line 48. Both capacitor banks will still discharge through HV-2 line 24 in response to the control signal on NPULSE-2 line 50, providing a pulse with an appropriate energy level.

While the embodiment described above employs two capacitor banks and two corresponding control signals to deliver the energy stored therein, the invention may usefully be practiced with three or more capacitor banks and output circuits under the control of three or more control signals. For example, in a system employing three capacitor banks linked by diodes corresponding to diode 100, the first control signal would trigger discharge of only the first capacitor bank. The second control signal would trigger discharge of the first and second capacitor banks, and the third control signal would trigger discharge of the first, second and third capacitor banks. Thus, the invention may readily be expanded to provide for a wide variety of simultaneous, sequential and single pulse regimens delivered using four or more electrodes.

For purposes of the following claims, the term "cardioverter" is used in its generic sense, indicating that the devices claimed are intended to treat cardiac arrhythmias including, but not limited to atrial and ventricular tachycardias and atrial and ventricular fibrillation.

In conjunction with the above disclosure, we claim:

1. A cardioverter comprising:
   means for coupling said cardioverter to at least first, second and third electrodes;
   first and second capacitor means for storing electrical energy;
   control means for generating first and second control signals; and
   pulse generating means, responsive to said first and second control signals for delivering only the energy stored in said first capacitor means between one of said first and second electrodes and said third electrode in response to said first control signal, and means for delivering energy stored in said first and second capacitor means between the other of said first and second electrodes and said third electrode in response to said second control signal.

2. A cardioverter according to claim 1 further comprising means for generating a third control signal and means for internally discharging the energy stored on said first and second capacitor means in response to said third control signal.

3. A cardioverter according to claim 1 wherein said control means comprises means for providing said second control signal subsequent to said first control signal.

4. A cardioverter according to claim 1 wherein said control means comprises means for simultaneously generating said first and second control signals.

5. A cardioverter according to claim 1 wherein said control means comprises means for generating said second control signal in the absence of said first control signal.

6. A cardioverter according to claim 1 wherein said means for coupling said cardioverter to said first, second and third electrodes comprises a connector assembly including at least three receptacles and further includes at least three electrode leads, each coupled to a different one of said three receptacles, each provided with a cardioversion electrode for location in, on or around the heart.

* * * * *